United States Patent [19]
Goldsteen et al.

[11] Patent Number: 5,931,842
[45] Date of Patent: Aug. 3, 1999

[54] METHODS AND APPARATUS FOR HANDLING TUBING USED IN MEDICAL PROCEDURES

[75] Inventors: David S. Goldsteen, Minneapolis; Thomas J. Bachinski, Lakeville; Daniel J. Sullivan, Medina, all of Minn.

[73] Assignee: Vascular Science Inc., Minneapolis, Minn.

[21] Appl. No.: 08/839,298

[22] Filed: Apr. 17, 1997

Related U.S. Application Data

[63] Continuation-in-part of application No. 08/745,618, Nov. 7, 1996.

[51] Int. Cl.$^6$ .................................................. A61F 11/00
[52] U.S. Cl. .................... 606/108; 606/151; 606/153; 623/1; 623/12
[58] Field of Search .................... 606/108, 151, 606/153, 191–200; 604/96–104; 623/1, 11, 12

[56] References Cited

U.S. PATENT DOCUMENTS

| | | | |
|---|---|---|---|
| 4,577,631 | 3/1986 | Kreamer. | |
| 4,592,754 | 6/1986 | Gupte et al. | 623/1 |
| 4,911,163 | 3/1990 | Fina | 606/108 |
| 5,331,975 | 7/1994 | Bonutti | 606/192 |
| 5,462,529 | 10/1995 | Simpson et al. | 604/101 |
| 5,464,449 | 11/1995 | Ryan et al. | 623/1 |
| 5,476,505 | 12/1995 | Limon | 606/198 |
| 5,569,296 | 10/1996 | Marin et al. | 606/198 |
| 5,571,086 | 11/1996 | Kaplan et al. | 604/96 |
| 5,676,670 | 10/1997 | Kim | 606/108 |

FOREIGN PATENT DOCUMENTS

| | | |
|---|---|---|
| 0 508 473 A2 | 10/1992 | European Pat. Off. . |
| WO 86/06285 | 11/1986 | WIPO . |
| WO 15582 A1 | 12/1990 | WIPO . |
| 0 649 637 A1 | 4/1995 | WIPO . |
| 0 723 786 A1 | 7/1996 | WIPO . |

*Primary Examiner*—Glenn K. Dawson
*Attorney, Agent, or Firm*—Fish & Neave; Robert R. Jackson; G. Victor Treyz

[57] ABSTRACT

Methods and apparatus are provided for attaching grafts of tubing between sites in a patient's body via the patient's existing arteries and veins. Grafts may be held in place during graft delivery using a partially inflated proximal balloon and a partially inflated distal balloon which frictionally engage axially spaced portions of the graft (e.g., pronged attachment rings that pierce the graft adjacent its ends). After aligning the distal end of the graft with the distal attachment site, the distal balloon may be further inflated to help attach the distal end of the graft to the distal attachment site (e.g., by driving the prongs of the distal attachment ring into the distal attachment site). The proximal balloon may then be inflated to attach the proximal end of the graft to the proximal attachment site. The insertion instrument allows the distance between the distal and proximal balloons to be adjusted, thereby accommodating grafts of various lengths. The separation between distal and proximal balloons may be fixed using a locking mechanism.

20 Claims, 6 Drawing Sheets

5,931,842

METHODS AND APPARATUS FOR HANDLING TUBING USED IN MEDICAL PROCEDURES

This is a continuation-in-part of copending application Ser. No. 08/745,618, filed Nov. 7, 1996.

BACKGROUND OF THE INVENTION

This invention relates to handling tubing used in medical procedures. For example, the invention may be used in connection with delivering and installing tubular grafts into a patient's body to repair, replace, or supplement a patient's natural body organ structures or tissues. The invention is especially useful in connection with inserting such grafts into a patient through the patient's existing arteries and veins.

Several procedures are known for revascularizing the human heart in order to treat a patient with one or more occluded coronary arteries. The earliest of these procedures to be developed involves exposing the heart by means of a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel such as a length of the patient's saphenous (leg) vein is harvested for use as a graft. The graft is used to create a new, uninterrupted channel between a blood source, such as the aorta, and the occluded coronary artery or arteries downstream from the arterial occlusion or occlusions.

A variation of the above procedure involves relocating a mammary artery of the patient to a coronary artery.

Although the above-described sternotomy procedures are increasingly successful, the high degree of invasiveness of these procedures and the requirement of these procedures for general anesthesia are significant disadvantages. Indeed, these disadvantages preclude use of sternotomy procedures on many patients.

More recently, less invasive procedures have been developed for revascularizing the heart. An example of these procedures is known as thoracostomy, which involves surgical creation of ports in the patient's chest to obtain access to the thoracic cavity. Specially designed instruments are inserted through the ports to allow the surgeon to revascularize the heart without the trauma of a midline sternotomy. Drugs may be administered to the patient to slow the heart during the procedure. Some thoracostomy procedures involve relocating a mammary artery to a coronary artery to provide a bypass around an occlusion in the coronary artery.

Thoracostomy bypass procedures are less traumatic than sternotomy bypass procedures, but they are still too traumatic for some patients. Also, the number of required bypasses may exceed the number of mammary arteries, thereby rendering thoracostomy procedures inadequate to fully treat many patients.

Another technique for revascularizing the human heart involves gaining access to the thoracic cavity by making incisions between the patient's ribs. his procedure is known as thoracotomy. It is also substantially less traumatic than midline sternotomy, but it is still too traumatic for some patients.

In view of the foregoing, even less traumatic approaches have been developed for revascularizing a patient, as described in Goldsteen et al. U.S. patent application Ser. No. 08/745,618, filed Nov. 7, 1996, and hereby incorporated by reference herein in its entirety. With such approaches, grafts (e.g., of saphenous veins) can be delivered to an operative site in the patient through the patient's existing arteries and veins. Grafts are typically inserted between two attachment sites in the patient's existing body organs (e.g., between a site along the patient's aorta and a site along the coronary artery downstream from a coronary artery occlusion).

A number of instruments are used to perform the different tasks associated with such a grafting procedure. One important instrument is the tubular graft insertion instrument used for graft delivery and attachment. Prior to insertion of the graft in the body, the graft is placed over the end of this instrument. Two small inflatable balloons, which are located a fixed distance from one another along the length of the instrument, are partially inflated to hold the graft in place. The graft is then inserted into the patient and aligned with the attachment site. When each end of the graft is aligned, the corresponding balloon is further inflated to drive prongs of a corresponding pronged attachment ring through the graft into the patient's tissue at the attachment site.

This type of graft insertion instrument can be used in a variety of situations. However, the fixed pacing between the two small balloons restricts the lengths of grafts that may be inserted with any given instrument. It is therefore an object of the present invention to provide methods and apparatus for inserting variable length grafts into a patient.

SUMMARY OF THE INVENTION

This and other objects of the invention are accomplished in accordance with the principles of the present invention by providing methods and apparatus in which grafts of various lengths are accommodated by a graft insertion instrument having balloons with a variable axial separation. The distance between the balloons can be adjusted to match the length of a given graft. The variable axial separation between balloons may then be substantially fixed using a securing or locking mechanism.

A preferred embodiment of the graft insertion instrument uses coaxial inner and outer tubes. The inner and outer tubes have associated inflatable annular or circumferential balloons. The balloons are partially inflated to frictionally engage respective axially spaced portions of the interior of the graft (e.g., pronged attachment rings at respective opposite ends of the graft). Prior to graft delivery, the graft may be held by the prongs of the attachment rings while the inner tube is moved within the outer tube to adjust the spacing of the balloons and attachment rings to match the length of the graft. During graft delivery, the spacing between the balloons is substantially fixed by the above-mentioned securing or locking mechanism, which substantially prevents slippage between the inner and outer tubes. Once the graft has been delivered to the attachment site, the balloons may be more fully inflated to drive the prongs on the attachment rings through the ends of the graft into the patient's tissue.

The foregoing is only illustrative of certain aspects of the invention, and further features of the invention, its nature and various advantages will be more apparent from the accompanying drawings and the following detailed description of the preferred embodiments.

DETAILED DESCRIPTION OF THE PREFERRED EMBODIMENTS

Figure 1:
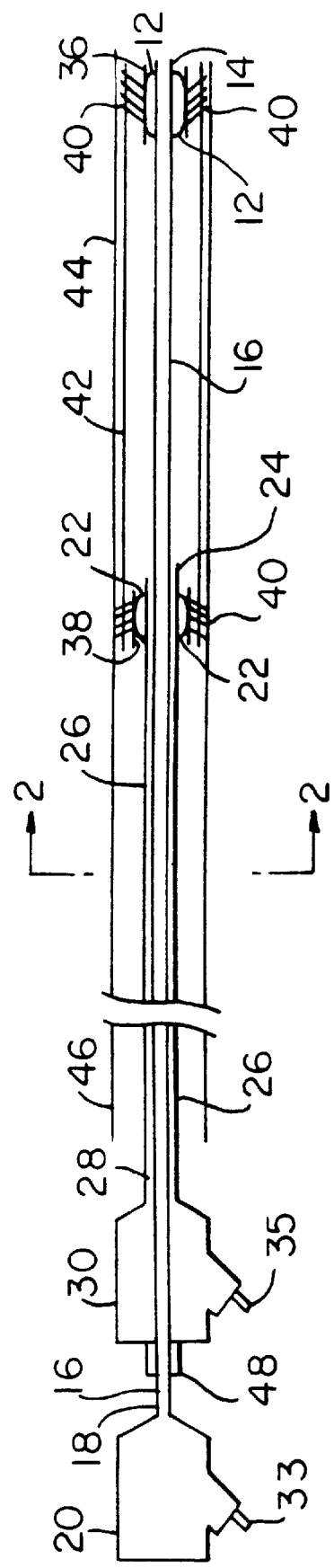
FIG. 1 is a simplified longitudinal sectional view showing a portion of illustrative tube handling apparatus in accordance with this invention.

An illustrative tube handling instrument 10 in accordance with the present invention is shown in FIG. 1. One possible use of instrument 10 is in connection with intralumenally delivering and installing graft tubing in a patient in need of such treatment. This type of use of instrument 10 will be discussed in detail in the immediately following portions of this specification, but it will be appreciated that the invention has many other possible uses, examples of which will be mentioned later in the specification.

In the illustrative instrument 10, balloon 12 is mounted to and extends circumferentially around the distal end 14 of inner tube 16. The proximal end 18 of inner tube 16 is attached to handle 20. Balloon 22 is mounted to and extends circumferentially around the distal end 24 of outer tube 26. The proximal end 28 of outer tube 26 is attached to handle 30.

Figure 2:
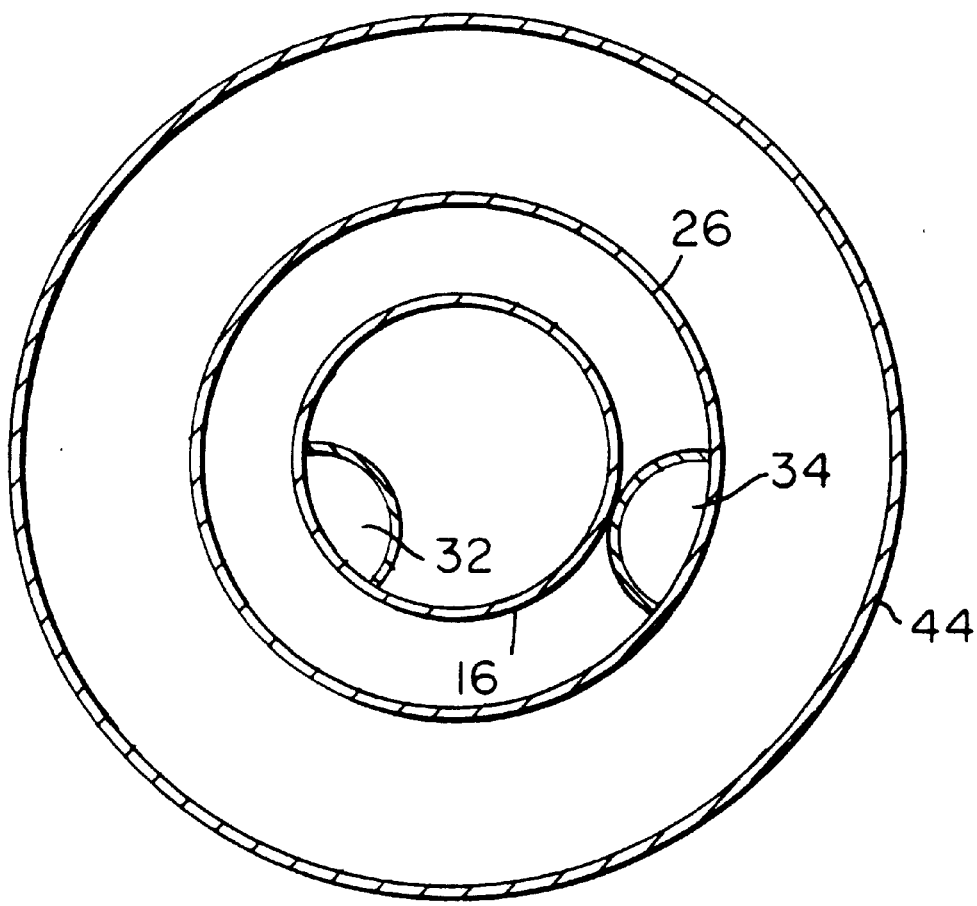
FIG. 2 is a cross-sectional view of the apparatus of FIG. 1 taken along the line 2—2 that shows the use of separate lumens for the inner and outer tubes.

As shown in FIG. 2, inner tube 16 has an associated lumen 32, which communicates with balloon 12. Balloon 12 may be inflated or deflated by controlling the introduction of pressurized gas or liquid (herein collectively called "fluid") through lumen 32. Outer tube 26 has an associated lumen 34, which communicates with balloon 22. Balloon 22 may be inflated or deflated by controlling the introduction of pressurized fluid through lumen 34. Pressurized fluid is introduced into lumen 32 via port 33 (FIG. 1). Port 35 (FIG. 1) in handle 30 is used to introduce fluid into lumen 34.

As shown in FIG. 1, balloons 12 and 22 may be partially inflated to hold the ends of graft tubing 42. For example, the partially inflated balloons frictionally engage respective attachment rings 36 and 38 on graft 42. Attachment rings 36 and 38 have prongs 40, which may pierce graft 42.

The graft assembly shown in FIG. 1 is preferably surrounded by delivery tube 44 prior to insertion in the patient's body. During insertion, the proximal portion of delivery tube 44 that contains graft 42 is inserted into a vein or artery of the patient via a standard catheter (not shown). Alternatively, tube 44 may itself be or perform the function of the catheter mentioned in the previous sentence. The physician can control the placement of delivery tube 44 by physically manipulating the proximal end 46 of delivery tube 44, which remains outside the patient's body. The physician can control placement of graft 42 by manipulating handles 20 and 30.

Graft 42 may be a length of natural tubing such as a harvested saphenous vein, artificial tubing, or a combination of such materials. Prior to insertion in the patient, graft 42 is typically cut to its desired final length by the physician. The axial separation between balloons 12 and 22 may be adjusted to accommodate the length of the graft by reciprocating inner tube 14 within outer tube 26 using handles 20 and 30. When the desired axial separation between balloons 12 and 22 has been achieved, locking mechanism 48 is engaged, thereby preventing or at least resisting further movement between balloons 12 and 22.

Figure 3:
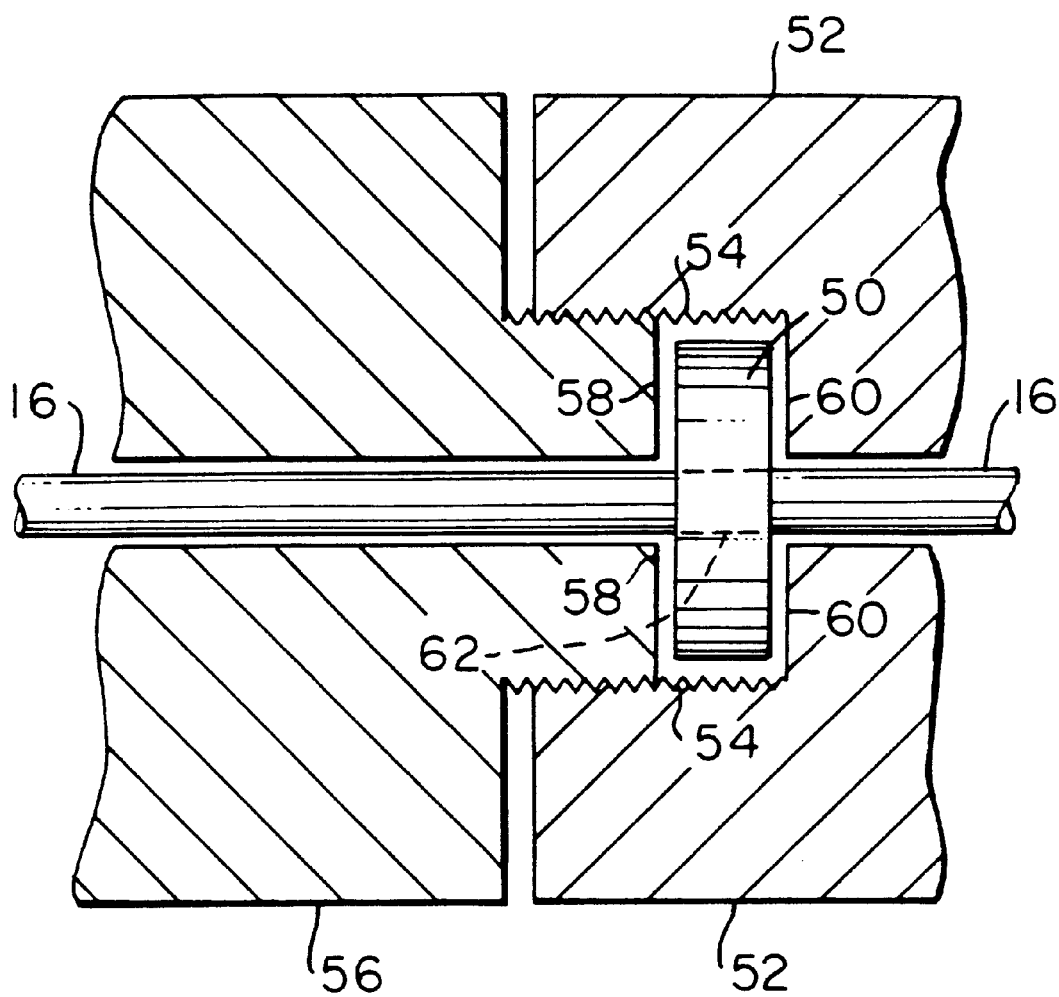
FIG. 3 is a side sectional view of an illustrative locking mechanism in accordance with the invention.

An illustrative locking mechanism 48 is shown in more detail in FIG. 3. In the unlocked configuration shown in FIG. 3, inner tube 16 reciprocates freely (left or right as viewed in FIG. 3) through an aperture in resilient ring 50. Member 52 is mounted to handle 30 (not shown in FIG. 3) and has threaded bore 54 for receiving threaded member 56. When it is desired to lock outer tube 26 to inner tube 16, member 56 is screwed into member 52, thereby axially compressing ring 50 between opposing end faces 58 and 60. The axial compression of ring 50 causes the inner diameter 62 of ring 50 to contract and frictionally engage inner tube 16. Because member 52 is attached to handle 30, which is attached to outer tube 26, engaging tube 16 with ring 50 prevents tube 16 from moving relative to tube 26.

The particular locking mechanism 48 shown in FIG. 3 is only illustrative, and any other suitable locking or securing structure may be used. One example of another locking mechanism is a set screw provided through handle 30 to selectively bear on inner tube 16 where it passes through handle 30. Another example of a locking mechanism is a clamp surrounding inner tube 16 and connected to outer tube 26. Tightening the clamp causes it to engage inner tube 16 and thereby lock tubes 16 and 26 together.

One of the advantages of instrument 10 is that it allows the physician to adjust the spacing between balloons 12 and 22 to accommodate grafts 42 of various lengths. In addition, using locking mechanism 48 to lock tubes 16 and 26 prevents relative movement between balloons 12 and 22. Preventing relative movement between balloons 12 and 22 ensures that graft 42 is not damaged by relative movement between balloons 12 and 22 during graft insertion and ensures that the distance between the ends of the graft (e.g., between attachment rings 36 and 38) is properly maintained. Locking the balloon spacing also ensures that the ends of graft 42 are separated by the proper amount for graft attachment.

Figure 4:
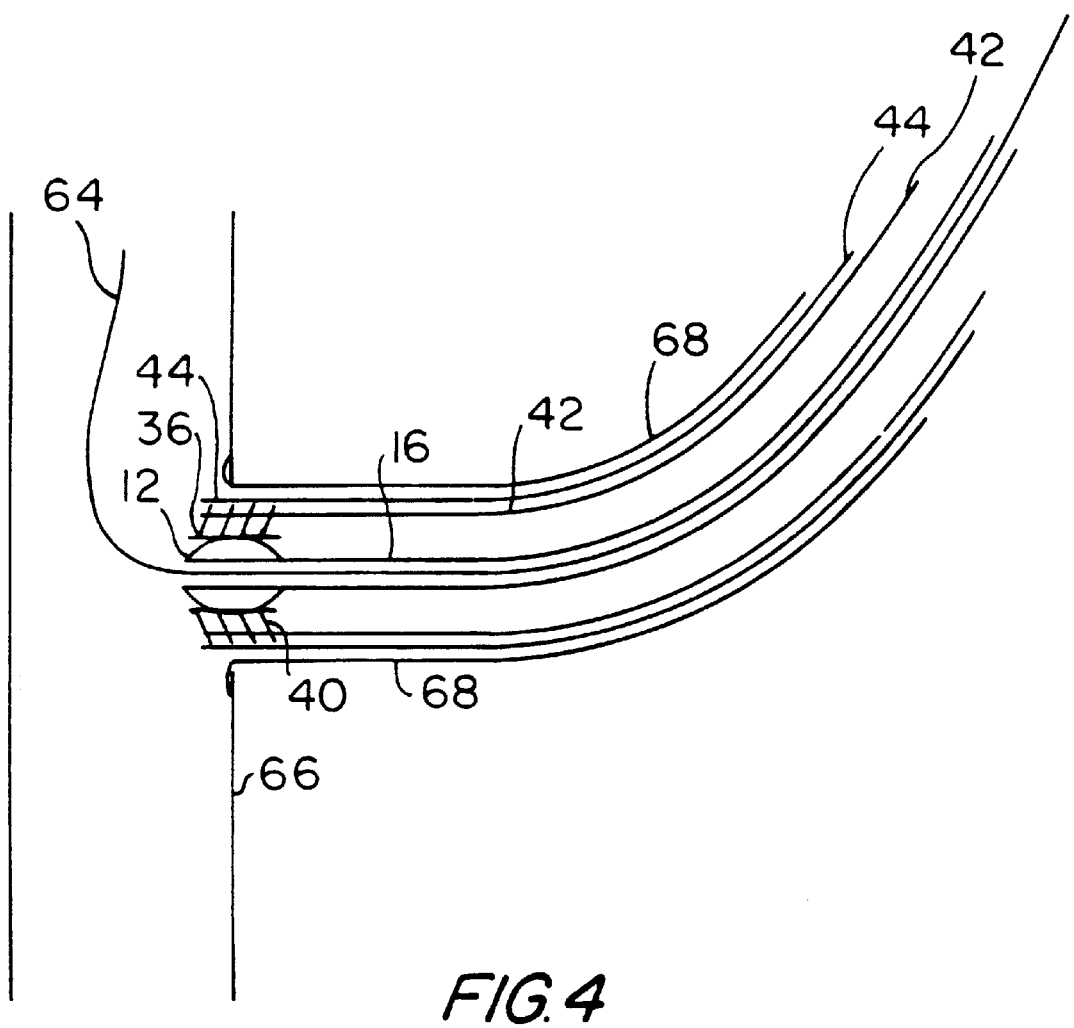
FIGS. 4–6 are diagrams illustrating the insertion of a natural graft to line a previously installed artificial graft.
Figure 5:
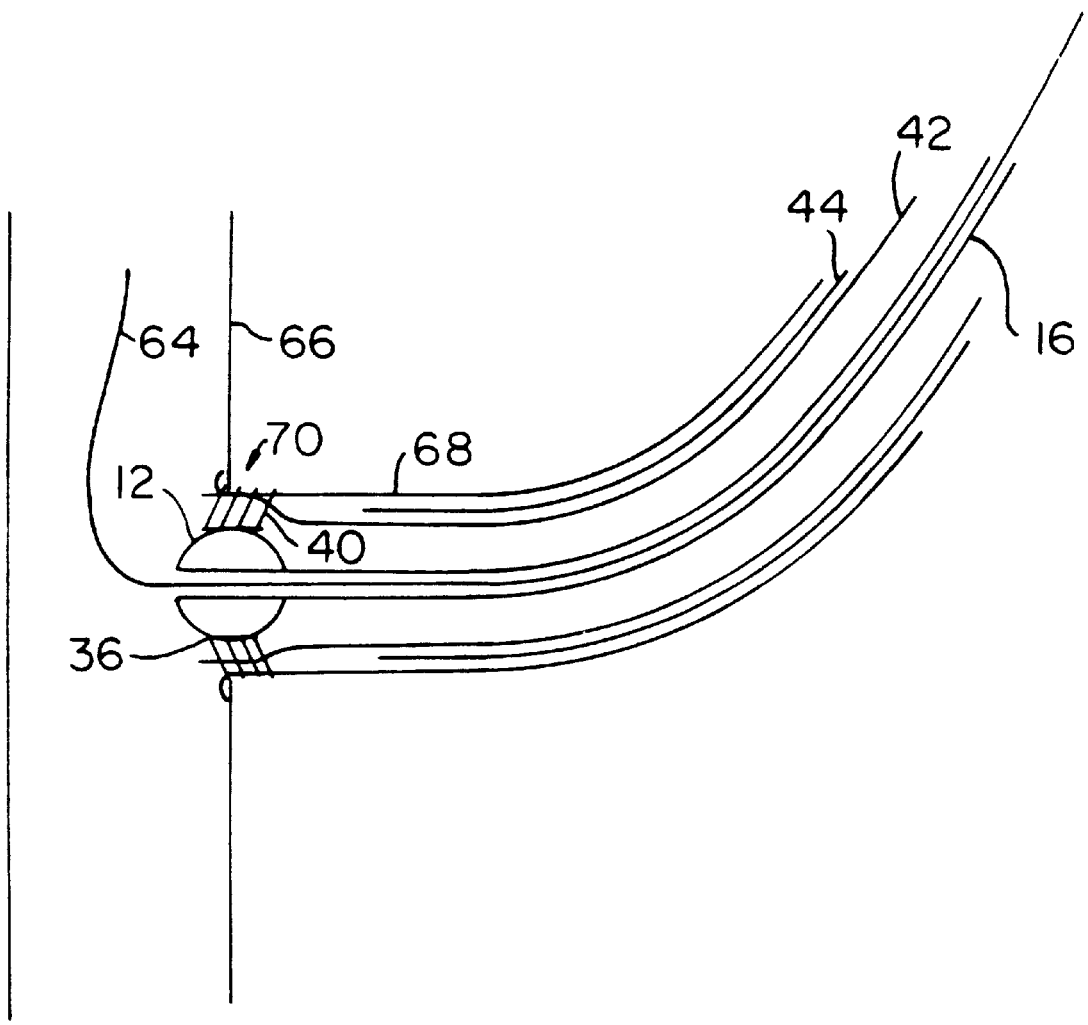
Figure 6:
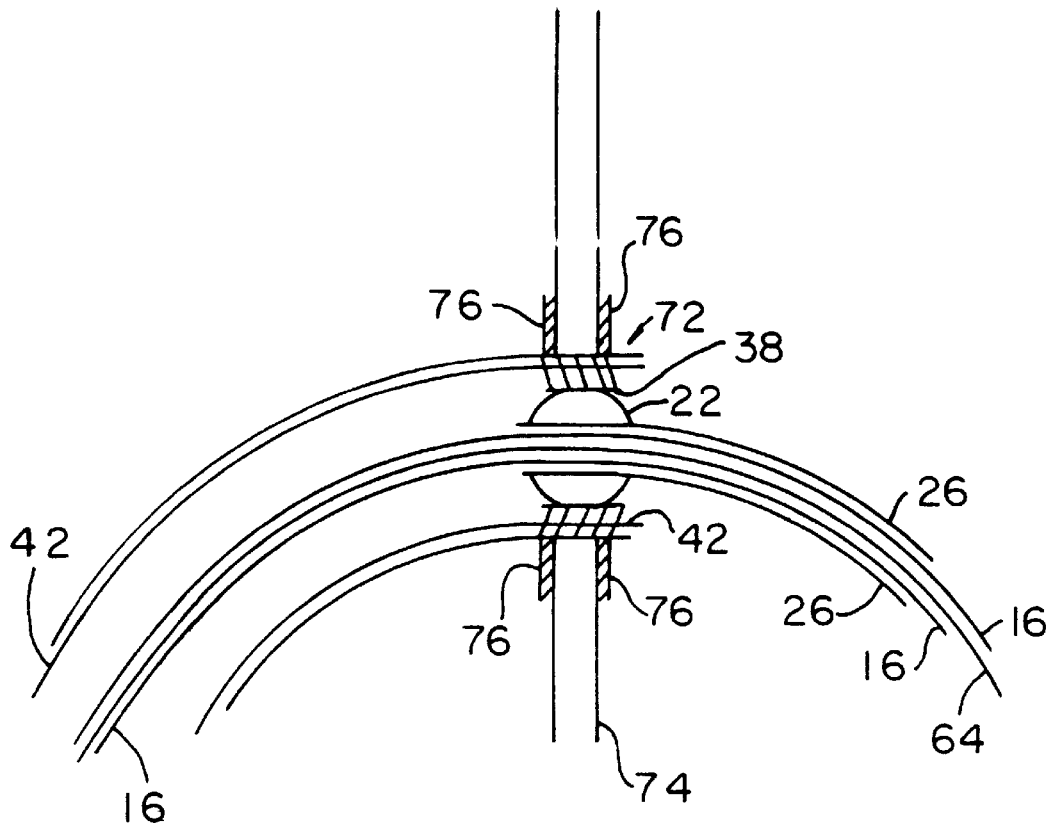

Part of an illustrative graft insertion procedure using instrument 10 is shown in FIGS. 4–6. The procedure shown in FIGS. 4–6 is a lining procedure in which a graft of natural tubing 42 (e.g., a length of harvested saphenous vein) is used to line a previously installed artificial tube 68 (e.g., to improve its bio-compatibility). However, it will be appreciated that similar graft insertion steps may be used to install various other types of tubing in a patient. For example, instrument 10 may be used for installing artificial tubing (either by itself or as a prelude to installing a lining of natural tubing), installing natural tubing by itself, simultaneously installing natural and artificial tubing (e.g., natural tubing concentrically inside artificial tubing), etc.

As shown in FIG. 4, a wire 64 may be used to guide the distal end of delivery tube 44 (e.g., into artery 66 via previously installed artificial graft 68). Wire 64 and graft 68 may have been previously installed using techniques described in the above-mentioned Goldsteen et al. reference. Delivery tube 44 and graft 42 (which is held by partially inflated balloons 14 and 22) are advanced along wire 64 through artificial graft 68 until prongs 40 of attachment ring 36 are adjacent to the intended distal site for graft attachment.

Once the distal end of graft 42 and attachment ring 36 have been properly aligned with the distal attachment site as shown in FIG. 4, delivery tube 44 is retracted in the proximal direction and balloon 12 is further inflated, as shown in FIG. 5. This step sets prongs 40 of ring 36 through graft 42 and artificial graft 68 into the tissue of artery 66 at attachment site 70.

After attaching the distal end of graft 42, delivery tube 44 is withdrawn in the proximal direction to expose proximal attachment ring 38, which is aligned with attachment site 72 for the proximal end of graft 42, as shown in FIG. 6. The proximal end of graft 42 is attached with ring 38 by further inflating balloon 22. The illustrative attachment site 72 shown in FIG. 6 is in aortal wall 74 and has previously installed axially spaced resilient flaps 76. The procedure is completed by deflating balloons 12 and 22 and withdrawing tubes 16, 26, and 44, and wire 64 from the patient's body.

To allow radiologic observation of instrument 10 during graft insertion, tubes 16, 26, and 44 may have radiologic (e.g., radio-opaque or fluoroscopically viewable) markers at suitable locations to help the physician place the structure where desired in the patient's body.

It will be understood that the foregoing is only illustrative of the principles of the invention, and that various modifications can be made by those skilled in the art without departing from the scope and spirit of the invention. For example, the use of balloons 12 and 22 as radially enlargeable structures is only illustrative, and other types of radially enlargeable structures (e.g., mechanically enlargeable structures) may be used if desired. The use of attachment rings like 36 and 38 is optional and such structures can be omitted if the procedure being performed does not require them. If structures like 36 and 38 are needed they can have any suitable construction, the particular construction shown and described herein being only one example.

The invention claimed is:

1. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering the tubing of a given length to a location in the patient's body through the patient's existing body tubing; and attaching the tubing of a given length to the patient's body organ tubing so that the tubing of a given length is at least partly outside the patient's existing body organ tubing.

2. The method defined in claim 1 wherein the first support structure is an inner tube and the second support structure is an outer tube, the method further comprising the step of reciprocating the inner tube within the outer tube.

3. The method defined in claim 1 wherein the first support structure contains a passage through which a wire is passed, the method further comprising the step of guiding the first and second support structures with the wire.

4. The method defined in claim 1 further comprising the steps of:

manipulating the first support structure with a first handle connected to the first support structure; and manipulating the second support structure with a second handle connected to the second support structure.

5. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering the tubing of a given length to a location in the patient's body through the patient's existing body tubing; and attaching the tubing of a given length to the patient's body organ tubing so that the tubing of a given length is at least partly outside the patient's existing body organ tubing;

wherein the distal structure comprises a distal inflatable balloon, and wherein the step of engaging a distal end of the tubing of a given length comprises inflating the distal inflatable balloon.

6. The method defined in claim 5 wherein the distal inflatable balloon extends circumferentially around the first support structure.

7. The method defined in claim 5 wherein the first support structure is an inner tube and the second support structure is an outer tube, the method further comprising the step of reciprocating the inner tube within the outer tube.

8. The method defined in claim 5 wherein the first support structure contains a passage through which a wire is passed, the method further comprising the step of guiding the first and second support structures with the wire.

9. The method defined in claim 5 further comprising the steps of:

manipulating the first support structure with a first handle connected to the first support structure; and manipulating the second support structure with a second handle connected to the second support structure.

10. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering the tubing of a given length to a location in the patient's body through the patient's existing body tubing; and grafting the tubing of a given length to the patient's body organ tubing so that the tubing of a given length is at least partly outside the patient's existing body organ tubing;

wherein the proximal structure comprises a proximal inflatable balloon, and wherein the step of engaging a proximal end of the tubing of a given length comprises inflating the proximal inflatable balloon.

11. The method defined in claim 10 wherein the proximal inflatable balloon extends circumferentially around the second support structure.

12. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure; and engaging a proximal end of the tubing of a given length with the proximal structure, wherein the tubing of a given length is a graft having a distal end to be attached to a distal attachment site within the patient's body, the distal structure includes an inflatable balloon, and a distal pronged attachment ring is provided to attach the graft;

frictionally engaging the distal pronged attachment ring by partially inflating the distal balloon during graft delivery;

holding the tubing of a given length with the prongs of the distal pronged attachment ring during graft delivery;

delivering the tubing of a given length to a location in the patient's body through the patient's existing body tubing; and attaching the tubing of a given length to the patient's body organ tubing so that the tubing of a given length is at least partly outside the patient's existing body organ tubing.

13. The method defined in claim 12 further comprising the step of driving the prongs of the distal pronged attachment ring through the graft and into the patient's tissue at the distal attachment site by further inflating the distal balloon during graft attachment.

14. A method for delivering tubing of a given length to be delivered to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure; and engaging a proximal end of the tubing with the proximal structure, wherein the tubing of a given length is a graft having a proximal end to be attached to a proximal attachment site within the patient's body, the proximal structure includes an inflatable balloon, and a proximal pronged attachment ring is provided to attach the graft;

frictionally engaging the proximal pronged attachment ring by partially inflating the proximal balloon during graft delivery;

holding the tubing of a given length with the prongs of the proximal pronged attachment ring during graft delivery;

delivering the tubing of a given length to a location in the patient's body through the patient's existing body tubing; and attaching the tubing of a given length to the patient's body organ tubing so that the tubing of a given length is at least partly outside the patient's existing body organ tubing.

15. The method defined in claim 14 further comprising the step of driving the prongs of the proximal pronged attachment ring through the graft and into the patient's tissue at the proximal attachment site by further inflating the proximal balloon during graft attachment.

16. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering the tubing of a given length to a location in the patient's body through the patient's existing body tubing; and attaching the tubing of a given length to the patient's body organ tubing so that the tubing of a given length is at least partly outside the patient's existing body organ tubing;

wherein:
the tubing of a given length is a graft having distal and proximal ends to be attached to respective distal and proximal attachment sites within the patient's body;
the distal and proximal structures include respective distal and proximal inflatable balloons;
distal and proximal pronged attachment rings are provided to attach the graft;
the distal and proximal pronged attachment rings are respectively frictionally engaged by partially inflating the distal and proximal balloons during graft delivery; and
the graft is held by the prongs of the distal and proximal pronged attachment rings during graft delivery.

17. The method defined in claim 16 wherein prongs of the distal and proximal pronged attachment rings are driven through the graft and into the patient's tissue at the distal and proximal attachment sites by further inflating the distal and proximal balloons during graft attachment.

18. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

placing a delivery tube over the first and second support structures and the tubing of a given length during delivery of the tubing of a given length;

delivering the tubing of a given length to a location in the patient's body through the patient's existing body tubing; and attaching the tubing of a given length to the patient's body organ tubing so that the tubing of a given length is at least partly outside the patient's existing body organ tubing.

19. A method for delivering tubing of a given length to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering pressurized fluid to the distal structure with a lumen contained within the first support structure;

delivering the tubing of a given length to a location in the patient's body through the patient's existing body tubing; and attaching the tubing of a given length to the patient's body organ tubing so that the tubing of a given length is at least partly outside the patient's existing body organ tubing.

20. A method for delivering tubing of a given length to be delivered to a location within a patient's body through the patient's existing body organ tubing using an instrument having first and second substantially longitudinal and axially aligned support structures, a distal structure mounted on the first support structure, and a proximal structure mounted on the second support structure, comprising the steps of:

adjusting the relative spacing between the distal and proximal structures to accommodate the given length of tubing by axially reciprocating the first and second support structures;

engaging a distal end of the tubing of a given length with the distal structure;

engaging a proximal end of the tubing of a given length with the proximal structure;

delivering pressurized fluid to the proximal structure with a lumen contained within the second support structure;

delivering the tubing of a given length to a location in the patient's body through the patient's existing body tubing; and attaching the tubing of a given length to the patient's body organ tubing so that the tubing of a given length is at least partly outside the patient's existing body organ tubing.

* * * * *